US008801178B2

(12) United States Patent
Mukai et al.

(10) Patent No.: US 8,801,178 B2
(45) Date of Patent: Aug. 12, 2014

(54) FUNDUS PHOTOGRAPHING APPARATUS

(75) Inventors: Hideo Mukai, Aichi (JP); Yoshihiko Yamada, Aichi (JP); Masaaki Hanebuchi, Aichi (JP)

(73) Assignee: Nidek Co., Ltd., Aichi (JP)

( * ) Notice: Subject to any disclaimer, the term of this patent is extended or adjusted under 35 U.S.C. 154(b) by 273 days.

(21) Appl. No.: 13/286,357

(22) Filed: Nov. 1, 2011

(65) Prior Publication Data
US 2012/0113389 A1 May 10, 2012

(30) Foreign Application Priority Data

Nov. 4, 2010 (JP) ................................ 2010-247900
Sep. 2, 2011 (JP) ................................ 2011-191292

(51) Int. Cl.
A61B 3/10 (2006.01)
A61B 3/14 (2006.01)
A61B 3/113 (2006.01)

(52) U.S. Cl.
CPC ................. *A61B 3/1015* (2013.01); *A61B 3/14* (2013.01); *A61B 3/113* (2013.01)
USPC ............. 351/205; 351/206; 351/209; 351/210

(58) Field of Classification Search
CPC ........ A61B 3/1015; A61B 3/14; A61B 3/152; A61B 3/113
USPC .......... 351/205, 206, 208, 209, 210, 221, 246
See application file for complete search history.

(56) References Cited

U.S. PATENT DOCUMENTS

| 5,777,719 A | 7/1998 | Williams et al. |
| 5,949,521 A | 9/1999 | Williams et al. |
| 6,095,651 A | 8/2000 | Williams et al. |
| 6,379,005 B1 | 4/2002 | Williams et al. |
| 8,419,187 B2 * | 4/2013 | Saito .............................. 351/206 |
| 2003/0025874 A1 | 2/2003 | Williams et al. |
| 2006/0044510 A1 | 3/2006 | Williams et al. |
| 2006/0170865 A1 | 8/2006 | Hirohara et al. |
| 2007/0291230 A1 * | 12/2007 | Yamaguchi et al. .......... 351/221 |
| 2008/0251955 A1 | 10/2008 | Williams et al. |
| 2008/0259273 A1 | 10/2008 | Williams et al. |
| 2008/0316429 A1 | 12/2008 | Williams et al. |

(Continued)

FOREIGN PATENT DOCUMENTS

| EP | 2322082 | 5/2011 |
| JP | 2001-507258 A | 6/2001 |
| JP | 2010-259543 A | 11/2010 |

OTHER PUBLICATIONS

Extended European Search Report dated Feb. 15, 2013 filed in the corresponding European Patent Application No. 12182454.4.

Primary Examiner — Huy K Mai
(74) Attorney, Agent, or Firm — Rankin, Hill & Clark LLP

(57) ABSTRACT

A fundus photographing apparatus includes a wavefront detecting optical system having a wavefront sensor for receiving reflection light from a fundus and measuring wavefront aberration of an eye, a wavefront compensating device for compensating the wavefront aberration, and a deviation detecting part for detecting deviation information corresponding to deviation between an effective region in which aberration compensation by the wavefront compensating device is effective, and a wavefront measuring region in which the wavefront aberration is measured by the wavefront detecting optical system, with respect to a direction perpendicular to an optical axial direction.

20 Claims, 9 Drawing Sheets

(56) References Cited

U.S. PATENT DOCUMENTS

2009/0002628 A1 1/2009 Williams et al.
2010/0277692 A1 11/2010 Mukai et al.
2011/0116044 A1 5/2011 Nozato et al.

* cited by examiner

FUNDUS PHOTOGRAPHING APPARATUS

CROSS-REFERENCE TO RELATED APPLICATION

This application claims priority from Japanese Patent Applications No. 2010-247900 filed on Nov. 4, 2010, and No. 2011-191292 filed on Sep. 2, 2011 with the Japan Patent Office, the entire contents of both of which are hereby incorporated by reference.

BACKGROUND

1. Technical Field

The present disclosure relates to a fundus photographing apparatus for photographing a fundus image of an examinee's eye in a state of compensating wavefront aberration of the examinee's eye.

2. Related Art

In an apparatus disclosed in, for example, JP-T-2001-507258, a wavefront sensor such as a Shack-Hartmann sensor detects wavefront aberration of an eye. Thereafter, based on the detection result, a wavefront compensating device is controlled. In addition, a fundus image after the wavefront compensation is photographed at a cell level. In such an apparatus, after completion of alignment of an examinee's eye with the apparatus, detection of wavefront aberration of the eye and wavefront compensating control based on the detection result are repeated.

SUMMARY

A fundus photographing apparatus includes a photographing optical system including a light source, an optical system for irradiating a fundus with light from the light source, and an optical system for receiving first reflection light from the fundus and photographing a fundus image. The fundus photographing apparatus also includes a wavefront detecting optical system having a wavefront sensor for receiving second reflection light from the fundus and measuring wavefront aberration of an eye, a wavefront compensating device disposed on an optical path of the photographing optical system for compensating the wavefront aberration by controlling a wavefront of incident light, and a deviation detecting part for detecting deviation information corresponding to deviation between an effective region and a wavefront measuring region with respect to a direction perpendicular to an optical axial direction. Aberration compensation by the wavefront compensating device is effective in the effective region, and the wavefront aberration is measurable by the wavefront detecting optical system in the wavefront measuring region.

DETAILED DESCRIPTION

Figure 1:
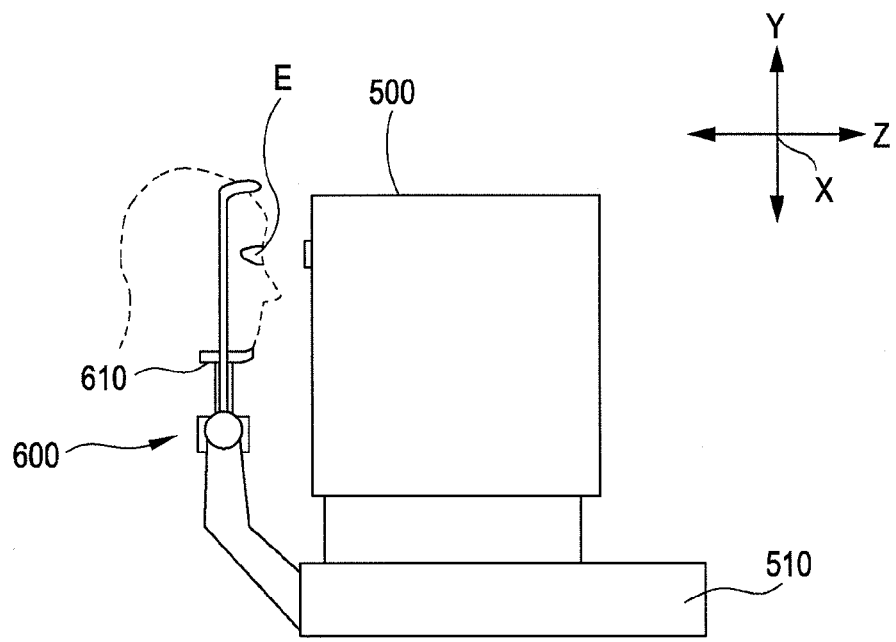
FIG. 1 is an external view of a fundus photographing apparatus according to an embodiment.

In the following detailed description, for purpose of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

After completion of alignment, a favorable fundus image may not be obtainable since a fixation state of an examinee's eye is not maintained sufficiently.

Figure 6A:
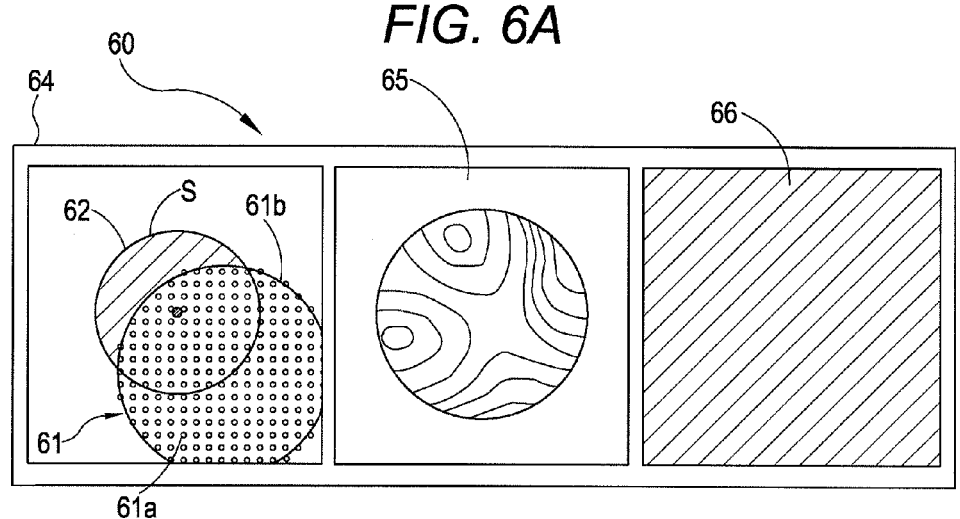
FIGS. 6A and 6B depict aberration compensating screens displayed on a screen of a monitor.

FIG. 6A is an example depicting a light-receiving result on a wavefront sensor in a state where a fixation position is positionally deviated. In this figure, a Hartmann image 61 received on the wavefront sensor and a circle 62, which is a region on the wavefront sensor corresponding to an effective region of a wavefront compensating device, are displayed to be overlapped. From a region S in the circle 62 that is not overlapped with the Hartmann image 61, a wavefront state is not detected. In this manner, in a case where a portion of the wavefront measuring data lacks (refer to FIG. 6A), information of the entire wavefront is not obtained. Thus, wavefront aberration in a wavefront compensating region is not measured appropriately. In a case where wavefront compensating control is performed on the basis of the detection result obtained in such a state, the wavefront compensating device will be controlled with an erroneous aberration-compensating amount.

Accordingly, in a case where a fixation position is positionally deviated, an examiner interrupts the measurement and retries alignment by adjusting positions of a chin rest and a forehead rest. Thus, the examiner is supposed to pay attention to deviation of the fixation position continuously. This leads to a longer time for the measurement.

Further, even when the lack of the wavefront measuring data is dealt with, it takes time to put the wavefront compensating device controlled with the erroneous aberration-compensating amount to an appropriate control state. Thus, it takes a considerable time (for example, about 3 seconds) until a favorable observation of the fundus image is resumed.

According to one technical aspect of the present disclosure, there is provided a fundus photographing apparatus (fundus photographing apparatus with wavefront compensation) enabling to photograph a favorable fundus image in which wavefront aberration has been compensated.

A fundus photographing apparatus according to an embodiment may be configured in the following manner.

This fundus photographing apparatus allows for photographing of a favorable fundus image in which wavefront aberration has been compensated.

Figure 9:
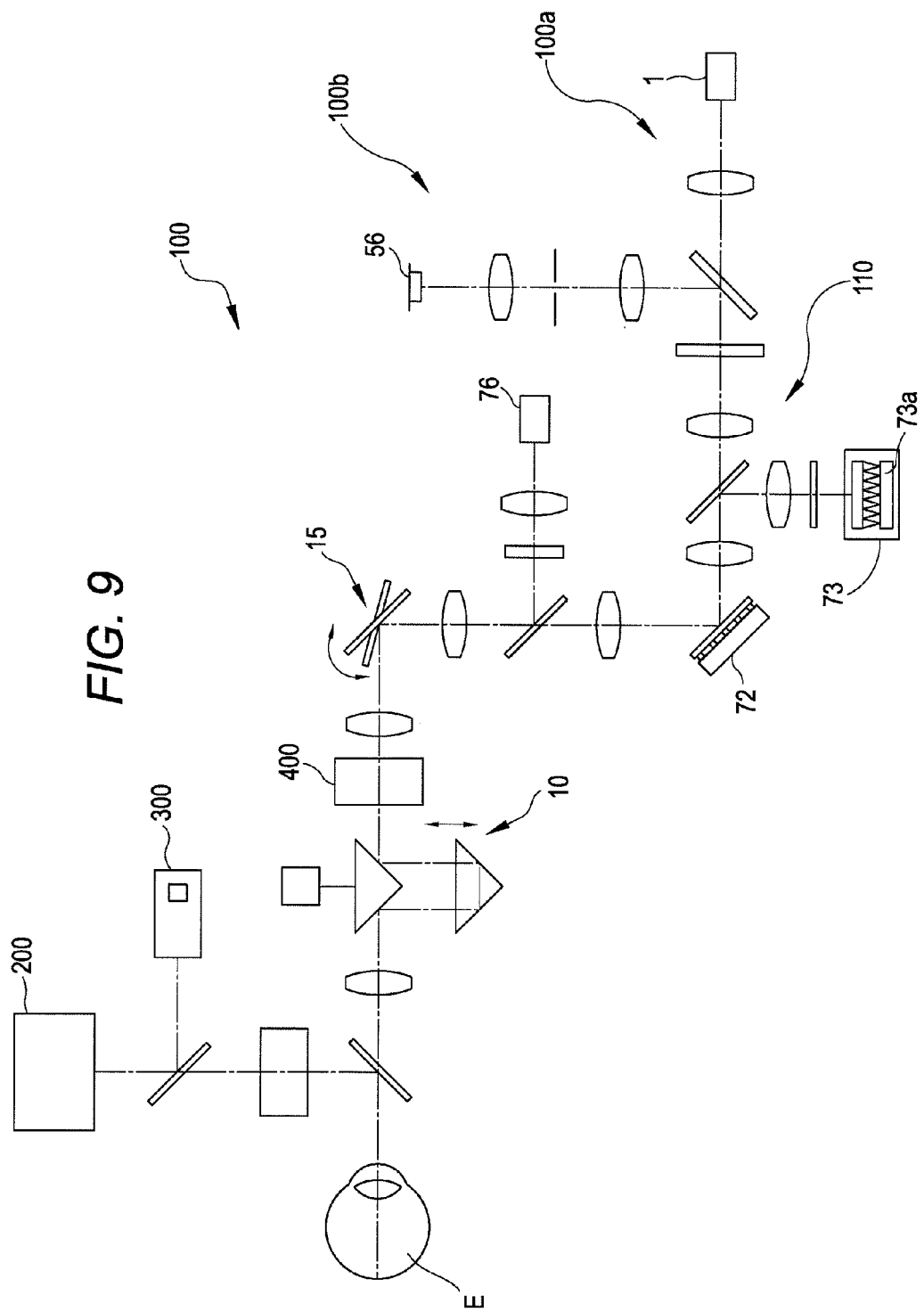
FIG. 9 is a schematic view of a modification example of an optical system of the fundus photographing apparatus.

Hereinafter, a fundus photographing apparatus (present apparatus) according to an embodiment is described. FIG. 1 is an external view of the present apparatus. The present apparatus includes a base table 510, a face supporting unit 600, and a photographing part 500. The face supporting unit 600 is attached to the base table 510. The photographing part 500 houses a later-described optical system and is disposed on the base table 510. The face supporting unit 600 is provided with a chin rest 610. The chin rest 610 is moved in the right-left direction (X direction), the up-down direction (Y direction), and the front-back direction (Z direction) with respect to a base part of the face supporting unit 600 by a not-shown chin rest driving part (chin rest driving means). In the following description, a mirror-type optical system is taken as an example of an optical system installed in the present apparatus. It is to be understood that the optical system installed in the present apparatus is not limited to this. For example, the present apparatus may be installed with a lens-type optical system (refer to FIG. 9) as well.

Figure 2:
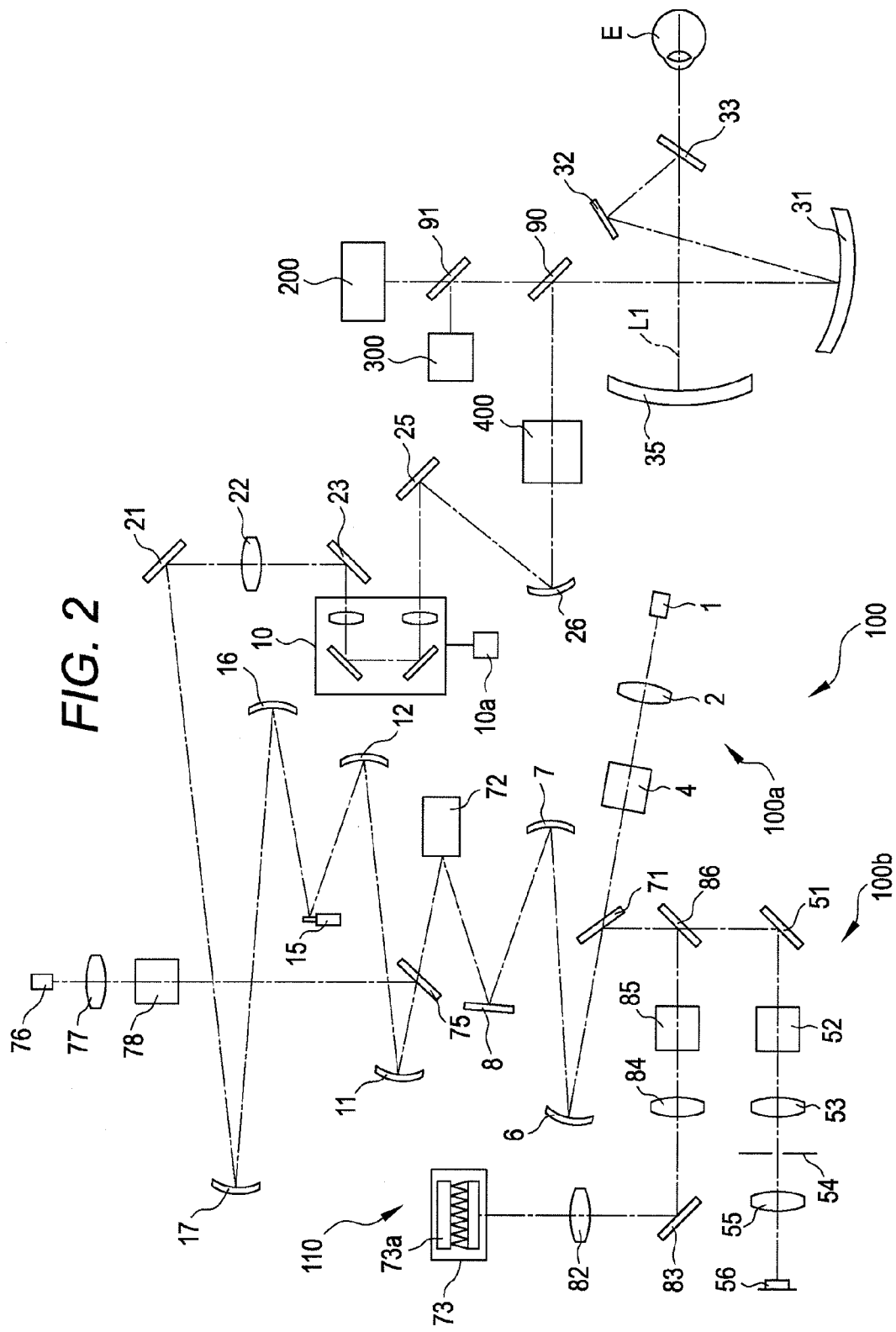
FIG. 2 is a schematic view of an optical system of this fundus photographing apparatus.

FIG. 2 is a schematic view of an optical system (mirror-type optical system) of the present apparatus. The present apparatus mainly includes a fundus photographing optical system 100, a wavefront aberration detecting optical system (hereinafter referred to as an aberration detecting optical system) 110, aberration compensating units (10 and 72), a second photographing unit 200, and a tracking unit (position detecting part) 300.

The fundus photographing optical system 100 receives reflection light (first reflection light) from a fundus of an examinee's eye E to photograph a fundus image of the examinee's eye. The aberration detecting optical system (aberration measuring optical system) 110 has a wavefront sensor 73. This aberration detecting optical system 110 projects measurement light to the fundus of the examinee's eye. The wavefront sensor 73 receives (detects) reflection light (second reflection light) from the fundus as a target pattern image. The aberration compensating units 10 and 72 are arranged in the fundus photographing optical system 100 to compensate aberration of the examinee's eye. The second photographing unit 200 obtains an observation image of the fundus (hereinafter referred to as a second fundus image). This second fundus image is an image to specify a photographing position of the fundus image obtained in the fundus photographing optical system 100 (hereinafter referred to as a first fundus image).

Herein, the fundus photographing optical system 100 photographs the fundus of the examinee's eye E at a high resolution and a high magnification. Further, the aberration compensating units 10 and 72 are roughly classified into a diopter scale compensating part 10 and a high-order aberration compensating unit (wavefront compensating device) 72. The diopter scale compensating part 10 compensates low-order aberration of the examinee's eye (diopter scale: e.g., spherical dioptic power). The wavefront compensating device 72 compensates high-order aberration of the examinee's eye.

The fundus photographing optical system 100 includes a first illumination optical system 100*a*, a first photographing optical system 100*b*, and the wavefront compensating device 72. The first illumination optical system 100*a* irradiates the examinee's eye E with illumination light (illumination light flux) to illuminate the fundus two-dimensionally. The first photographing optical system 100*b* receives reflection light (reflection light flux) of the illumination light emitted to the fundus to obtain the first fundus image. The fundus photographing optical system 100 is, for example, a scanning laser ophthalmoscope that includes a confocal optical system.

The first illumination optical system 100*a* includes a light source 1 (first light source) and a scanning part 15. The light source 1 emits the illumination light to illuminate the fundus. This illumination light is illumination light within a near infrared wavelength range that is hardly visually perceived by the examinee's eye. In the present embodiment, the light source 1 is an SLD (Super Luminescent Diode) light source with a wavelength of 840 nm. It is to be noted that the light source 1 may be any light source as long as it emits spot light having a property of strong convergence. The light source 1 may be, for example, a semiconductor laser. The scanning part 15 scans the fundus in the horizontal direction (X direction) by the illumination light (spot light).

First, the first illumination optical system 100*a* is described. The first illumination optical system 100*a* includes a lens 2, a polarizing beam splitter (PBS) 4, a concave mirror 6, a concave mirror 7, a planar mirror 8, the wavefront compensating device 72, a concave mirror 11, a concave mirror 12, the scanning part 15, a concave mirror 16, and a concave mirror 17. These are disposed on an optical path from the light source 1 to the fundus. The first illumination optical system 100*a* further includes a planar mirror 21, a lens 22, a planar mirror 23, the diopter scale correcting part 10, a planar mirror 25, a concave mirror 26, a deflecting part 400, a dichroic mirror 90, a concave mirror 31, a planar mirror 32, a planar mirror 33, and a concave mirror 35. These are also disposed on the aforementioned optical path. The diopter scale correcting part 10 has planar mirrors and lenses. The deflecting part 400 scans the fundus in the vertical direction (Y direction) with the illumination light emitted from the light source 1. The deflecting part 400 further corrects a scanning position of the illumination light used in two-dimensional scanning. The dichroic mirror 90 makes optical paths of the second photographing unit 200 and other units approximately coaxial with the optical path of the first illumination optical system 100*a*.

The illumination light emitted from the light source 1 is made into parallel light by the lens 2 and reaches the PBS 4. In the present embodiment, the illumination light is made into a light flux simply having an S-polarized component by the PBS 4. The illumination light after passing through the PBS 4 passes through a beam splitter (BS) 71 is reflected by the concave mirror 6, the concave mirror 7, and the planar mirror 8, and then enters the wavefront compensating device 72. The illumination light reflected by the wavefront compensating device 72 is reflected by the concave mirror 11 and the concave mirror 12 via a BS 75, and then heads for the scanning part 15.

The scanning part 15 scans the fundus in the X direction with the illumination light. In the present embodiment, the scanning part 15 includes a resonant mirror and a driving part to drive the mirror. The resonant mirror is a deflection member to scan the fundus with the illumination light deflected in the horizontal direction (X direction). The illumination light after passing through the scanning part 15 is reflected by the concave mirror 16, the concave mirror 17, and the planar mirror 21, and is condensed by the lens 22. Subsequently, the illumination light is reflected by the planar mirror 23. The illumination light passes through the diopter scale correcting part 10, is reflected by the planar mirror 25 and the concave mirror 26, and heads for the deflecting part 400. Furthermore, the diopter scale correcting part 10 includes a driving part 10*a*. The diopter scale correcting part 10 is capable of varying its optical path length by moving the planar mirrors and the lenses in the arrow directions indicated in FIG. 2 by the driving part 10*a*. Specifically, the diopter scale correcting part 10 functions to correct a diopter scale. It is to be noted that the diopter scale correcting part 10 may include the driving part and a prism that is movable in the optical axial direction by the driving part.

The deflecting part 400 scans the fundus in the X and Y directions with the illumination light. In the present embodiment, the deflecting part 400 includes two galvano mirrors, i.e., a galvano mirror for X scanning and a galvano mirror for Y scanning. The illumination light after passing through the deflecting part 400 is reflected by the dichroic mirror 90, the concave mirror 31, the planar mirror 32, the planar mirror 33, and the concave mirror 35 and is condensed by the fundus of the examinee's eye E. In this manner, the scanning part 15 and the deflecting part 400 scan the fundus two-dimensionally with the illumination light.

The dichroic mirror 90 has a property of transmitting light fluxes from the later-described second photographing unit 200 and tracking unit 300 and reflecting light fluxes from the light source 1 and a later-described light source 76. Furthermore, the positions of the emitting ends of the light source 1 and the light source 76 are in a conjugate relation with the position of the fundus of the examinee's eye E. The first illumination optical system 100a for two-dimensionally irradiating the fundus with the illumination light is configured as above.

The tracking unit 300 detects a temporal change in positional deviation caused by, for example, fine involuntary movement of the examinee's eye E being subjected to photographing and obtains information on the movement position. The tracking unit 300 sends to a control part 80 a light-receiving result obtained at the start of the tracking as criterion information. The tracking unit 300 thereafter sends to the control part 80 a light-receiving result (light-receiving information) per scanning in succession. The control part 80 compares the light-receiving information obtained after the start of the tracking with the criterion information. The control part 80 finds information on the movement position using an arithmetical operation in order to obtain light-receiving information that is the same as the criterion information. Based on the obtained movement position information, the control part 80 drives the deflecting part 400. The tracking as described above allows the deflecting part 400 to be driven such that fine involuntary movement of the examinee's eye E may be offset. Thus, the fundus images displayed on a monitor 70 are prevented from moving. Further, a dichroic mirror 91 has properties of transmitting a light flux from the second photographing unit 200 and reflecting a light flux from the tracking unit 300.

Next, the first photographing optical system 100b is described. The first photographing optical system 100 shares the optical path from the dichroic mirror 90 to the BS 71 with the first illumination optical system 100a. The first photographing optical system 100 further includes a planar mirror 51, a PBS 52, a lens 53, a pinhole plate 54, a lens 55, and a light-receiving device 56. Furthermore, in the present embodiment, the light-receiving device 56 is an APD (Avalanche Photodiode). The pinhole plate 54 is placed at a conjugate position with the fundus.

Reflection light obtained by the reflection of the illumination light that has been emitted from the light source 1 from the fundus travels in the first illumination optical system 100a in the reverse direction, is reflected by the BS 71 and the planar mirror 51, and is transmitted through the PBS 52. Thus, the reflection light becomes light simply having the S-polarized component. This light comes into focus at the pinhole of the pinhole plate 54 through the lens 53. The reflection light in focus at the pinhole is received on the light-receiving device 56 through the lens 55. Furthermore, a portion of the illumination light is reflected from the cornea of the eye. However, a large part of the corneal reflection light is removed by the pinhole plate 54. Thus, the corneal reflection light has a reduced adverse effect on the obtained image of the corneal reflection. Thus, the light-receiving device 56 is capable of receiving the reflection light from the fundus with reduced influence of the corneal reflection.

The first photographing optical system 100b is configured as above. The image that is obtained by processing the reflection light received by the first photographing optical system 100b is the first fundus image. The first fundus image of one frame is formed by main scanning by the scanning part 15 and sub scanning by the galvano mirror for Y scanning provided in the deflecting part 400. Angles at which the mirrors of the scanning part 15 and the deflecting part 400 are swung (swing angles) are set such that a fundus image with a given view angle may be obtained by the first photographing unit 100. The view angle is set to about 1 to 5 degrees herein such that a predetermined area of the fundus may be observed and photographed under a high magnification (e.g., observed and photographed at a cell level). In the present embodiment, the view angle is 1.5 degrees. A photographed area of the first fundus image is on the order of 500 µm square, depending on the diopter scale of an examinee's eye or other factors.

Moreover, reflection angles of the galvano mirror for X scanning and the galvano mirror for Y scanning provided in the deflecting part 400 are significantly moved by the view angle at which the first fundus image is photographed. This causes a photographing position of the first fundus image on the fundus to be changed.

Next, the second photographing unit 200 is described. The second photographing unit 200 is arranged to obtain a fundus image with a view angle wider than the view angle of the first photographing unit (i.e., the second fundus image). The obtained second fundus image is used to specify and find the photographed portion of the fundus at which the first fundus image with the narrow view angle is obtained. The second photographing unit 200 arranged to obtain the second fundus image obtains a fundus image of the examinee's eye E with a wide view angle (for example, about 20 to 60 degrees) in real time so as to be used as an image for observation. An observation and photographing optical system used in an existing fundus camera, or an optical system and a control system used in an existing scanning laser ophthalmoscope (SLO) may be used for the second photographing unit 200.

Next, the aberration detecting optical system 110 is described. As described above, some optical devices of the aberration detecting optical system 110 are disposed on the optical path of the first illumination optical system 100a. That is, the aberration detecting optical system 110 shares a portion of the optical path with the first illumination optical system 100a. The aberration detecting optical system 110 includes the light source 76, a lens 77, a PBS 78, the BS 75, the BS 71, a dichroic mirror 86, a PBS 85, a lens 84, a planar mirror 83, a lens 82, and the wavefront sensor 73. The aberration detecting optical system 110 shares the optical members from the BS 71 to the concave mirror 35 that are disposed on the optical path of the first illumination optical system 100a with the first illumination optical system 100a.

The wavefront sensor 73 includes, for example, a microlens array including multiple microlenses, and a two-dimensional photographing device 73a (two-dimensional light-receiving device) arranged to receive the light fluxes transmitted through the microlens array. The light source 76 that defines a light source for aberration detection (a third light source) is a light source for emitting light within an infrared wavelength range that is different from the light emitted from the light source 1. In the present embodiment, the light source 76 is a laser diode arranged to emit laser light with a wavelength of 780 nm.

The laser light emitted from the light source 76 is made into a parallel light flux by the lens 77. This light flux is made into polarized light (P-polarized light) by the PBS 78 so as to have a polarization direction perpendicular to the polarization direction of the illumination light emitted from the light source 1. This polarized light is directed to the optical path of the first illumination optical system by the BS 75. Furthermore, the position of the emitting end of the light source 76 is in a conjugate relation with the fundus conjugate position. The PBS 78 makes the polarization direction of the light emitted from the light source 76 a predetermined direction. The PBS 78 functions as a first polarizing part (first polarizing means) of the wavefront compensating part.

The laser light reflected by the BS 75 is collected on the fundus of the examinee's eye E through the optical path of the first illumination optical system 100a. The laser light reflected from the fundus is reflected by the wavefront compensating device 72 through the optical members of the first illumination optical system 100a. This reflected light deviates from the optical path of the first illumination optical system 100a by the BS 71 and is then reflected by the dichroic mirror 86. This reflected light is guided to the wavefront sensor 73 through the PBS 85, the lens 84, the planar mirror 83, and the lens 82.

The PBS 85 defines a second polarizing part (second polarizing means) of the wavefront compensating part. The PBS 85 shields the light (i.e., the P-polarized light) emitted from the light source 76 to the eye E. On the other hand, the PBS 85 transmits the polarized light having the polarization direction perpendicular to the polarization direction of the P-polarized light (i.e., the S-polarized light) and guides it to the wavefront sensor 73. The dichroic mirror 86 has a property of transmitting the light from the light source 1 with a light wavelength of 840 nm and reflecting the light from the light source 76 for aberration detection with a light wavelength of 780 nm. Thus, the wavefront sensor 73 is arranged to detect the light having the S-polarized component among the scattered light obtained by the scattering of the emitted laser light from the fundus. Thus, the light reflected from the cornea and the light reflected by the optical devices are restricted from being detected by the wavefront sensor 73.

The scanning part 15, the reflection surface of the wavefront compensating device 72, and the microlens array of the wavefront sensor 73 are approximately in conjugate relations with a pupil of the examinee's eye. A light-receiving surface of the wavefront sensor 73 is approximately in a conjugate relation with the fundus of the examinee's eye E. The wavefront sensor 73 is a device capable of detecting wavefront aberration such as low-order aberration and high-order aberration. Examples of the wavefront sensor 73 include a Shack-Hartmann sensor and a wavefront curvature sensor for detecting change in light intensity.

The wavefront compensating device 72 is, for example, a liquid-crystal spatial optical modulator. The wavefront compensating device 72 may be reflective LCOS (Liquid Crystal On Silicon). The wavefront compensating device 72 is arranged on the optical path of the fundus photographing optical system 100. The wavefront compensating device 72 controls the wavefront of the incident light to compensate the wavefront aberration of the examinee's eye. The wavefront compensating device 72 is disposed in an orientation such that it can compensate aberration of predetermined linear polarized light (S-polarized light). Examples of this S-polarized light are the illumination light from the light source 1 (S-polarized light), the illumination light reflected from the fundus (S-polarized light), and the reflection light of the light for wavefront aberration detection (S-polarized light component). Having such a configuration, the wavefront compensating device 72 modulates the light having the S-polarized component among the light entering the wavefront compensating device 72.

The wavefront compensating device 72 includes a liquid crystal layer having a configuration such that the direction in which liquid crystal molecules are arrayed in approximately parallel to a polarization plane of the light entering the wavefront compensating device 72. To be specific, the wavefront compensating device 72 is disposed such that a predetermined plane rotated in accordance with the change in voltage applied to the liquid crystal layer may be approximately parallel to a predetermined plane. This predetermined plane is a plane that includes the axes of the reflection light from the fundus entering and reflecting from the wavefront compensating device 72 and the normal to a mirror layer of the wavefront compensating device 72.

In the present embodiment, the wavefront compensating device 72 is a liquid-crystal modulator and, for example, reflective LCOS (Liquid Crystal On Silicon). However, the present disclosure is not limited thereto, and the wavefront compensating device 72 has only to be a reflective wavefront compensating device. For example, a deformable mirror that is a form of MEMS (Micro Electro Mechanical Systems) may be used as the wavefront compensating device 72. Alternatively, the wavefront compensating device 72 need not be a reflective wavefront compensating device. For example, the wavefront compensating device 72 may be a transmissive wavefront compensating device, which is arranged to transmit the reflection light from the fundus and compensate wavefront aberration thereof.

In the present embodiment, the light source arranged to emit the illumination light having the wavelength different from the wavelength of the light emitted from the first light source is used as the light source for aberration detection. However, the first light source may be used as the light source for aberration detection.

In the present embodiment, the wavefront sensor and the wavefront compensating device are at conjugate positions with the pupil of the examinee's eye. However, the wavefront sensor and the wavefront compensating device have only to be approximately at conjugate positions with a certain portion (e.g., cornea) of the anterior segment of the examinee's eye.

Figure 3:
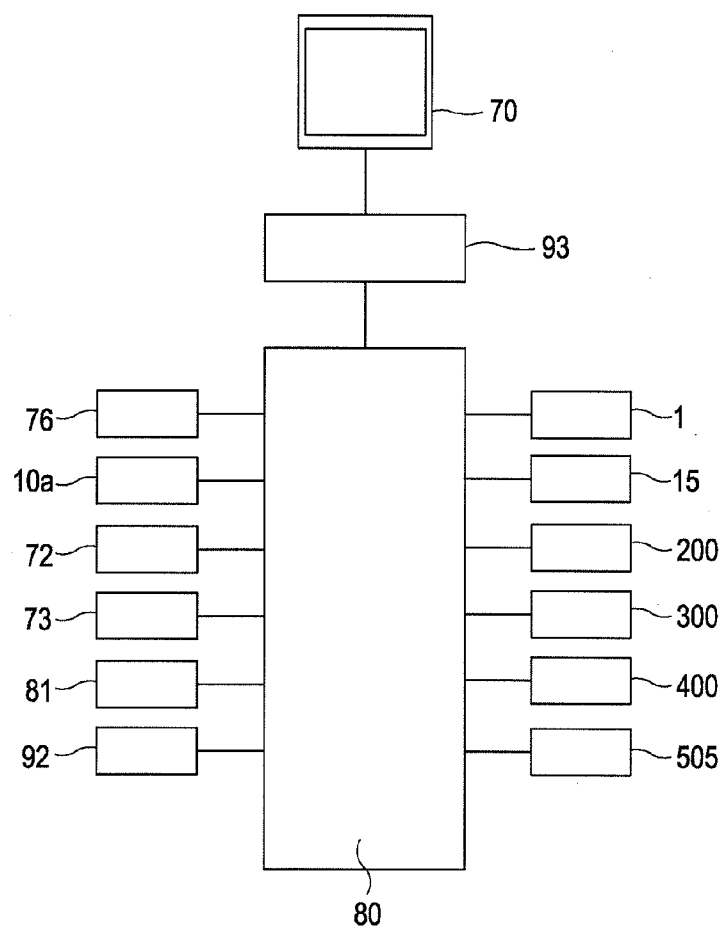
FIG. 3 is a block diagram of a control system of this fundus photographing apparatus.

Next, a control system of the present apparatus is described. FIG. 3 is a block diagram of the control system of the present apparatus. A control part 80 arranged to perform the control of the entire apparatus is connected with the light source 1, a driving mechanism 505, the scanning part 15, the light-receiving device 56, the wavefront compensating device 72, the wavefront sensor 73, the light source 76, the second photographing unit 200, the tracking unit 300, the deflecting part 400, and the driving part 10a. The control part 80 is also connected with a memory part 81, a control part 92, an image processing part 93, and the monitor 70.

The image processing part 93 displays images of the examinee's fundus with different view angles, to be specific, the first fundus image and the second fundus image, on the monitor 70 based on light received at the light-receiving device 56 and the second photographing unit 200. The memory part 81 is arranged to store various setting information and photographed images. It is to be noted that the monitor 70 is a monitor of an external personal computer or a monitor provided in the present apparatus. The monitor 70 is arranged to display the fundus images (first and second fundus images) that are renewed at a given frame rate. The frame rate is, for example, 10 to 100 Hz. Thus, the fundus images are displayed as moving images. In the present embodiment, the control part 80 functions also as a display control part of the monitor 70, a driving control part of the deflecting part 400, and emission control units of the light sources 1 and 76 and other devices.

The wavefront compensating device 72 is controlled based on the wavefront aberration detected by the wavefront sensor 73. Thus, high-order aberration of the S-polarized component in the reflection light of the light for wavefront aberration detection and high-order aberration of the illumination light emitted from the light source 1 and reflection light thereof are removed. In this manner, high-order aberration possessed by the illumination light emitted from the light source 1 and the reflection light thereof is removed. In other words, the first fundus image of the examinee's eye E at a high resolution is obtained in which the high-order aberration is removed (the wavefront aberration is compensated). In this case, the diopter scale compensating part 10 compensates low-order aberration.

Figure 4:
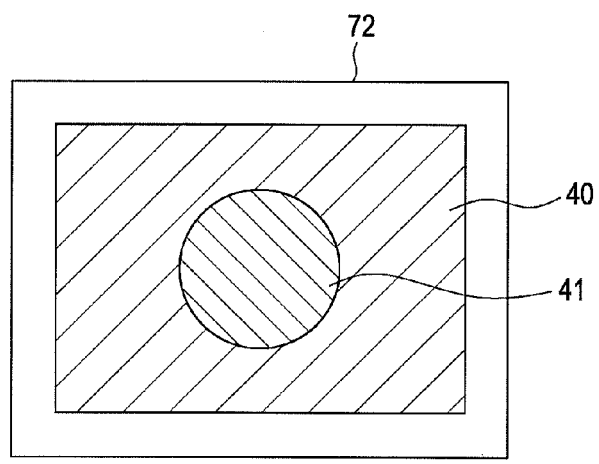
FIG. 4 is an explanatory view of a compensable region and an effective region.

FIG. 4 is an explanatory view of a compensable region and an effective region of the wavefront compensating device 72. A compensable region 40 is a region in which the wavefront of incident light is controllable for the wavefront compensating device 72. An effective region 41 is a region in the compensable region 40 in which aberration compensation (wavefront compensation) by the wavefront compensating device 72 is effective. This aberration compensation is conducted by performing feedback control of the wavefront compensating device 72 based on a detection signal from the wavefront sensor 73. In the present embodiment, the dimensions of the compensable region 40 are 16×12 mm. The diameter of the effective region 41 is 8.64 mm. The compensable region 40 is sufficiently larger than the effective region 41. Thus, at least the position, the dimensions, or the shape of the effective region 41 is changeable in the compensable region 40 (described later in detail).

Figure 5A:
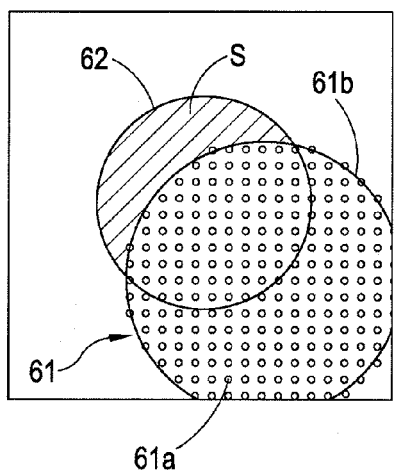
FIGS. 5A and 5B are explanatory views of specific examples of a target pattern image and an effective region.
Figure 5B:
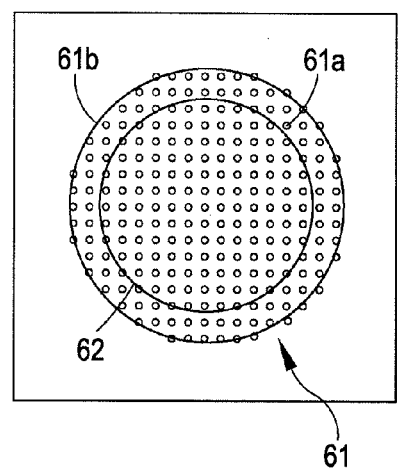
Figure 6B:
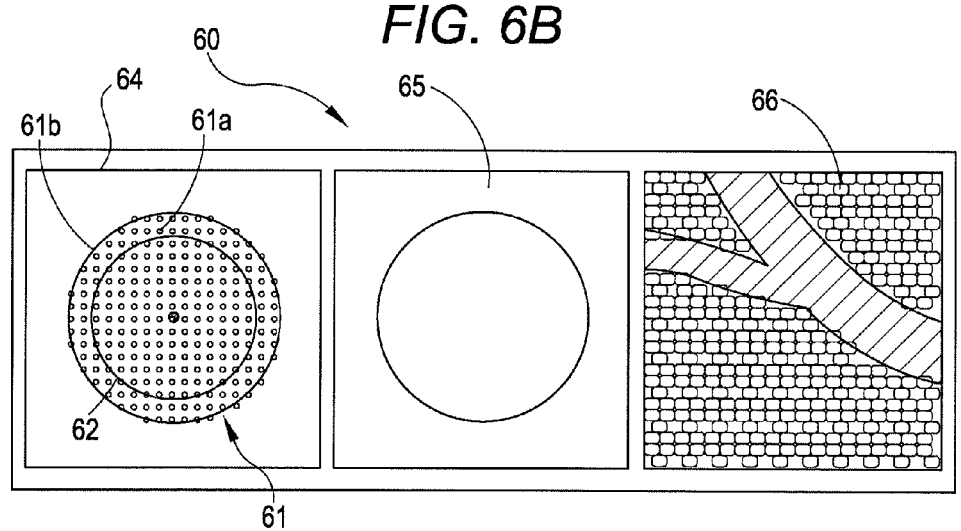

FIGS. 5A and 5B are explanatory views of specific examples of a target pattern image and an effective region. FIGS. 6A and 6B depict aberration compensating screens 60 displayed on the screen of the monitor 70. On the aberration compensating screen 60 are displayed a target pattern image 61, an aberration compensating graphic 65, and a cell image 66. The target pattern image 61 is an image received on the two-dimensional photographing device 73a of the wavefront sensor 73. In the present embodiment, this image is a Hartmann image. Hereinafter, the target pattern image is described as the Hartmann image as well. The aberration compensating graphic 65 is an image to graphically display the degree of aberration compensation (remaining aberration). The cell image 66 is a cell image of the fundus photographed actually.

The Hartmann image (dot pattern image) 61 is a cluster of plural dot images 61a received on the wavefront sensor 73. Fundus reflection light passing through the lens array is received on the two-dimensional photographing device 73a of the wavefront sensor 73 and is photographed as a Hartmann image. The Hartmann image 61 is then displayed on the monitor 70. Aberration can be detected in a region at which the dot images 61a are detected by the wavefront sensor 73.

A circle 62 is a region (virtual region) on the wavefront sensor (two-dimensional photographing device 73a) corresponding to an effective region of the wavefront compensating device 72. In FIG. 6A, the circle 62 and the Hartmann image 61 are displayed to be overlapped on the monitor 70. A mark located at the center of the circle 62 corresponds to a central position of the effective region of the wavefront compensating device 72.

An outer circumference and a region of the circle 62 and information of the position of the circle 62 on the wavefront sensor 73 are set in the memory part 81 in advance. These can be derived in advance by a calibration or a simulation. Furthermore, light entering the effective region of the wavefront compensating device 72 is limited to a portion (e.g., light reflected in a region having a diameter of 6 mm on the pupil) of the entire light entering the wavefront compensating device 72. Thus, the other portion of the entering light is reflected toward the light-receiving device 54, but wavefront thereof is not compensated.

Aberration compensation is performed based on an aberration detection result by the wavefront sensor 73. More specifically, in a region of the circle 62 overlapping with the Hartmann image 61, a wavefront state is detectable (refer to FIG. 5B). On the other hand, in a region S in the circle 62 in which no Hartmann image 61 is formed, a wavefront state is not detected. In a case where the wavefront data (Hartmann image 61) is partly missing (in a case where the circle 62 is deviated from the Hartmann image 61), information of the entire wavefront is not obtained. Thus, wavefront aberration in a wavefront compensating region is not measured appropriately (refer to FIG. 5A). Therefore, as shown in FIG. 6A, even when aberration compensation is executed, aberration is not removed appropriately as shown in the aberration compensating graphic 65. Further, as shown in the cell image 66, photographing the cell image is difficult.

Figure 7:
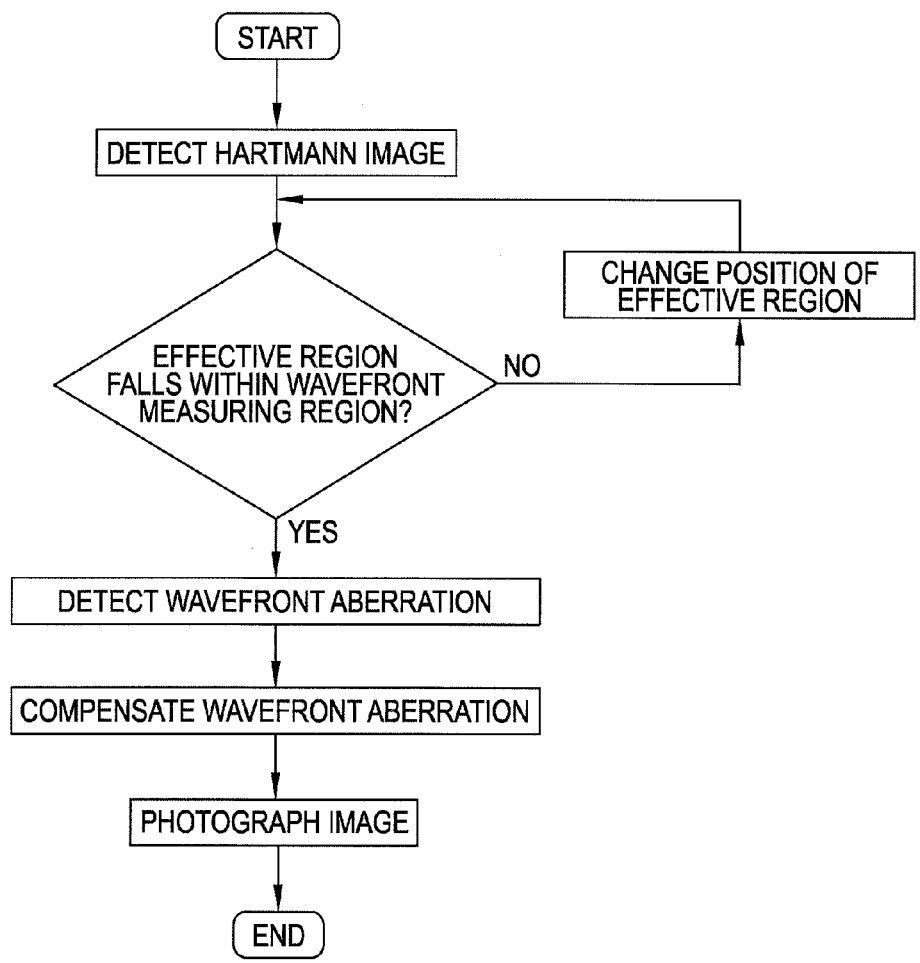
FIG. 7 is a flowchart of operations of the fundus photographing apparatus.

Operations of the present apparatus configured as above are described with reference to the flowchart of FIG. 7.

First, the examiner adjusts the position of the chin rest 610 manually or automatically while observing a not-shown anterior segment image displayed on the screen of the monitor 70. Thus, rough alignment (relative positional adjustment between the eye E and the photographing part 500 (aberration detecting optical system 110)) is performed. The examiner also instructs the examinee to fixate a not-shown fixation target.

After completion of the rough alignment by using the chin support 610, the examiner selects a not-shown measurement switch. The control part 80 thereby performs diopter scale correction by using the diopter scale correcting part 10. Subsequently, the control part 80 detects wavefront needed for aberration compensation.

Subsequently, the control part 80 detects deviation information. This deviation information corresponds to deviation between a region of the wavefront sensor 73 corresponding to the effective region of the wavefront compensating device 72 (e.g., the circle 62) and a region in the wavefront sensor 73 for receiving a target pattern image (e.g., the Hartmann image 61) (wavefront measuring region). The control part 80 then adjusts the position of the chin rest 610 so as to eliminate (compensate) this deviation (to place the deviation information in an allowable range). It is to be noted that, in a case where the present apparatus is configured to allow the photographing part 500 to be moved with respect to the eye E, the control part 80 may cause the photographing part 500 to be moved so as to place the deviation information within the allowable range.

For example, the control part 80 determines whether or not the circle 62 falls within an outer circumference 61b of the Hartmann image 61 (Hartmann image outer circumference 61b; wavefront measuring region). In a case where the circle 62 deviates from the Hartmann image outer circumference 61b, the control part 80 adjusts relative positions of the eye E and the photographing part 500 so that the circle 62 falls within the Hartmann image outer circumference 61b. On the other hand, in a case where the circle 62 falls within the Hartmann image outer circumference 61b, the control part 80 detects wavefront aberration of the examinee's eye E based on a detection result by the wavefront sensor 73. The control part 80 further starts photographing the fundus by the fundus photographing optical system 100.

The control part 80 calculates an aberration-compensating amount based on an aberration detection result of the examinee's eye E. The control part 80 controls a position of the effective region 41 of the wavefront compensating device 72 based on the calculation result to compensate the wavefront aberration. The control part 80 then newly obtains a Hartmann image outputted from the wavefront sensor 73 and detects wavefront aberration. The control part 80 then calculates an aberration-compensating amount based on the aberration detection result. The control part 80 controls the position of the effective region 41 of the wavefront compensating device 72 based on the calculation result to compensate the wavefront aberration. In the above manner, the control part 80 performs feedback control in which aberration detection and control of wavefront compensation based on the result are repeated. For example, in a case where the wavefront compensating device 72 is LCOS, the feedback control to a phase pattern for compensation is performed by loop processing including detection of wavefront aberration by the wavefront sensor 73, calculation of a phase pattern of the LCOS based on this detection result, and voltage application to pixels of the LCOS based on this calculation result. Thus the refractive index of the liquid crystal layer of the LCOS changes occasionally based on the detection result of the wavefront aberration. Therefore, distortion in the wavefront of the fundus reflection light is corrected.

Further, in a case where the wavefront compensating device 72 is a deformable mirror, the feedback control to a shape of the entire mirror is performed by loop processing including detection of wavefront aberration by the wavefront sensor 73, calculation of a mirror shape based on this detection result, and voltage application to driving parts of the deformable mirror based on this calculation result. Thus, the shape of the entire mirror changes occasionally based on the detection result of the wavefront aberration. Therefore, distortion in the wavefront of the fundus reflection light is corrected.

The above feedback control is reflected on a fundus moving image that is acquired while the wavefront aberration is compensated. That is, by performing the above feedback control, the wavefront of the fundus reflection light is compensated. Thus, blur of the fundus moving image is reduced. Therefore, even when an aberration state of the examinee's eye against the present apparatus (photographing part 500) is changed along with changes in the fixation state and position of the examinee's eye, a clear fundus image is acquired.

Furthermore, the feedback control is performed until the end of photographing. Further, when a predetermined trigger signal is outputted during the feedback control and the acquisition of the fundus moving image, a cell image of the fundus acquired at the time is stored on the memory part 81 as a moving image or a still image.

Even after the alignment is done by movement of the chin rest 610 or the photographing part 500, and the acquisition of an image is started as described above, there is a case in which positional deviation occurs between the examinee's eye E and the present apparatus (photographing part 500) due to, for example, insufficiently maintained fixation state. In this case, a wavefront measuring region of the wavefront sensor 73 (region in the Hartmann image outer circumference 61b) actually used in wavefront measurement may deviate from a region (circle 62) of the wavefront sensor 73 corresponding to the effective region 41 of the wavefront compensating device 72 (both the regions may positionally deviate from each other). In this case, information of the entire wavefront is not obtained. Thus, wavefront aberration in the wavefront compensating region is not measured appropriately.

Hereinafter, description is given of control operations for a case where the wavefront measuring region of the wavefront sensor 73 deviates from the region (circle 62) of the wavefront sensor 73 corresponding to the effective region 41 of the wavefront compensating device 72 after the start of the image acquisition operation.

It is to be noted that the deviation between the two regions on the wavefront sensor 73 corresponds to deviation between the wavefront measuring region of the wavefront sensor 73 and the effective region of the wavefront compensating device 72 with respect to a direction perpendicular to the optical axial direction. Thus, in the following description, this deviation is also referred to as deviation between the wavefront measuring region of the wavefront sensor 73 and the effective region of the wavefront compensating device 72.

Hereinafter, description is given of control operations for a case where the wavefront measuring region deviates from the effective region of the wavefront compensating device 72. In a case where the wavefront measuring region and the effective region of the wavefront compensating device deviate from each other, the control part 80 controls the wavefront compensating device 72 to compensate the deviation between the effective region 41 in which aberration compensation by the wavefront compensating device 72 is effective, and the wavefront measuring region which is a region in which wavefront aberration is measured by the aberration detecting optical system 110, with respect to a direction perpendicular to the optical axial direction. For example, the control part 80 detects information on deviation between the effective region 41 and the wavefront measuring region with respect to the direction perpendicular to the optical axial direction. In a case where detected deviation information is out of an allowable range, the control part 80 then adjusts the position of the effective region 41 so that the deviation information falls within the allowable range.

To be specific, the control part 80 first detects positions of dot images received at the outermost side in the Hartmann image 61 received on the wavefront sensor 73 sequentially. The control part 80 thereby detects positional information of the Hartmann image outer circumference 61b. Thus, the region of the Hartmann image 61 (wavefront measuring region) is derived.

Subsequently, the control part 80 compares the positional information of the Hartmann image outer circumference 61b with the positional information of the circle 62 (effective region). The control part 80 determines based on this comparison result whether or not the wavefront measuring region fills the effective region. Thus, whether or not aberration of the eye E is compensable is determined.

More specifically, the control part 80 compares the region surrounded by the Hartmann image outer circumference 61b (refer to the dotted line) with the region surrounded by the circle 62. In a case where the region surrounded by the circle 62 falls within the region surrounded by the Hartmann image outer circumference 61b, the control part 80 determines that it is sufficient (OK) (refer to FIG. 5B). Further, in a case where the region surrounded by the circle 62 does not fall within the region surrounded by the Hartmann image outer circumference 61b, the control part 80 determines that it is insufficient (NG) (refer to FIG. 5A).

When the control part 80 determines that it is NG, the control part 80 controls the wavefront compensating device 72 so that the circle 62 falls within the Hartmann image outer circumference 61b. In other words, the control part 80 changes the position of the effective region 41 in the compensable region 40 of the wavefront compensating device 72. The compensable region 40 is a region in which the wavefront of incident light is controllable (such as movement or enlargement). Therefore, by changing the position to control the wavefront of incident light, the position of the effective region 41 is changeable (resettable) in the compensable region 40.

Figure 8A:
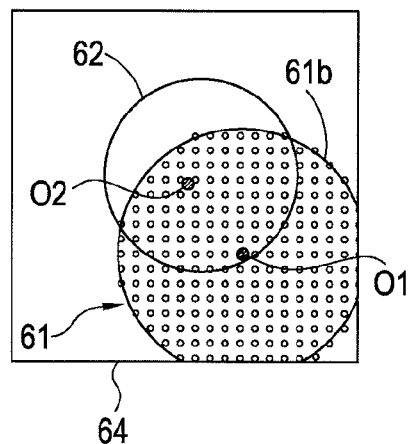
FIGS. 8A and 8B are explanatory views of specific examples of changes in position of the effective region.
Figure 8B:
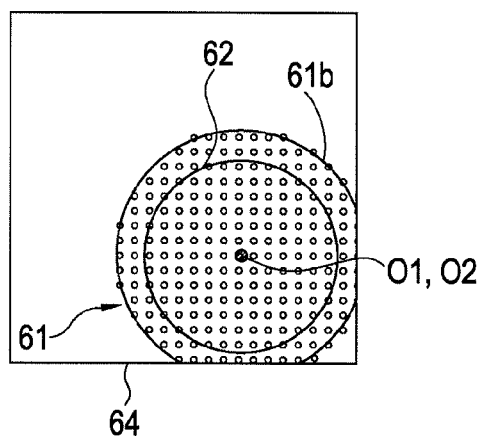

Hereinafter, a specific example of changes in position of the effective region is described with reference to FIGS. 8A and 8B. For example, the control part 80 calculates center coordinates O1 of the Hartmann image 61 based on the detected positional information of the Hartmann image outer circumference 61b. The control part 80 also calculates center coordinates O2 of the circle 62 (refer to FIG. 8A). The control part 80 changes the position to control the wavefront by the wavefront compensating device 72 so as to obtain match between the coordinate position of the center coordinates O1 of the Hartmann image 61 and the coordinate position of the center coordinates O2 of the circle 62. Thus, the position of the effective region 41 is moved. Therefore, as depicted in FIG. 8B, the circle 62 falls within the Hartmann image outer circumference 61a. This enables aberration compensation. Further, as depicted in FIG. 6B, the aberration compensating graphic 65 is in a state where aberration has been removed. Moreover, the cell image 66 is an image in which aberration has been removed.

The examinee's eye may move occasionally. To deal with this, the control part 80 causes the position of the effective region 41 of the wavefront compensating device 72 to track changes in measurable region against the measurement optical axis.

Furthermore, along with the aforementioned positional adjustment of the circle 62 (effective region 41), the control part 80 performs aberration compensation control for a case where the effective region is a second effective region after positional adjustment by using an aberration compensation state for a case where the effective region is a first effective region before positional adjustment. After moving the effective region to the second effective region, the control part 80 performs as aberration compensation control the feedback control in which aberration detection and control of wavefront compensation based on the detection result are repeated. That is, the control part 80 adopts an aberration-compensating amount for the effective region 41 before positional adjustment as an aberration-compensating amount for the effective region 41 after positional adjustment. In other words, the control part 80 performs compensation processing in which the aberration compensating position is changed while the aberration-compensating amount is maintained.

For example, the control part 80 causes the memory part 81 to store an aberration-compensating amount immediately before the circle 62 is deviated from the Hartmann image outer circumference 61b (or at a point in time prior to the deviation), for adjusting the position of the effective region 41. Subsequently, at the same time as completion of positional adjustment of the circle 62, the control part 80 operates the wavefront compensating device 72 with the aberration-compensating amount stored on the memory part 81. It is to be understood that, in a case where the aberration-compensating amount is maintained at the time of changing the position of the effective region, an original aberration-compensating amount need not be stored. The wavefront compensating device 72 has only to be operated with an aberration-compensating amount on which an aberration detection result before the circle 62 is deviated from the Hartmann image outer circumference 61b is reflected. In other words, similar driving signals to those before the circle 62 is deviated from the Hartmann image outer circumference 61b have only to be sent to the wavefront compensating device 72.

In a case where the wavefront compensating device 72 is LCOS, the control part 80 may adjust the position of the effective region 41 and set the voltage amount to be applied to pixels of the LCOS in the effective region 41 in order to keep the refractive index of the LCOS constant to the voltage amount before the circle 62 deviates from the Hartmann image outer circumference 61b. Similarly, in a case where the wavefront compensating device 72 is a deformable mirror, the control part 80 may set the voltage amount to be applied to driving parts in order to keep the shape of the entire mirror constant in the effective region to the voltage amount before the circle 62 deviates from the Hartmann image outer circumference 61b.

Even in a case where the deviation information is out of the allowable range, the control part 80 operates the fundus photographing optical system 100 to obtain high-magnification images of the fundus successively. Additionally, the control part 80 outputs the obtained high-magnification images to the monitor 85 occasionally as moving images. That is, the control part (tracking system) 80 causes the effective region of the wavefront compensating device 72 to track the Hartmann image. In other words, the effective region tracks the Hartmann image.

After adjusting the position of the circle 62, the control part 80 detects wavefront aberration by the wavefront sensor 73. The control part 80 also sends driving signals based on the aberration detection result to the wavefront compensating device 72. The control part 80 repeats the aberration detection by the wavefront sensor 73 and the wavefront compensation by the wavefront compensating device 72 based on the detection result while the circle 32 falls within the outer circumference 31a. Thus, aberration detection results detected in real time are reflected on the wavefront compensating device 72. Therefore, favorable high-magnification fundus images with less blur are obtained.

Wavefront aberration is compensated in the above manner. Thereafter, when a predetermined trigger signal is outputted, a cell image of the fundus is photographed as a moving image or a still image.

Furthermore, there is a case in which the Hartmann image 61 is significantly deviated from the compensable region 64 of the wavefront compensating device 72 by the significant deviation of the position of the pupil of the examinee's eye. At this time, the examiner can recognize the fact that the position of the examinee's eye is significantly deviated, for example, by generating an alarm sound or displaying on the screen of the monitor 70 a message indicating that the position of the examinee's eye is significantly deviated. In this case, the examiner performs rough alignment again by adjusting the position of the chin rest 610. Therefore, the Hartmann image 61 is allowed to fall within the compensable region 64 of the wavefront compensating device 72.

With the above configuration, in a case where aberration information of the eye E is not obtainable due to changes in position of the pupil of the examinee's eye, deviation of the measurement position is compensated. Thus, a minute region of the fundus is photographable smoothly and favorably. Further, the examiner need not pay attention to changes in position of the pupil of the examinee's eye continuously. Therefore, the examiner's trouble and burden are alleviated.

Further, in the present apparatus, even in a case where the position of the effective region is changed, the feedback control for aberration compensation is started by using an aberration-compensating amount of the wavefront compensating device 72 before the position of the effective region is changed as an initial value. Thus, it takes less time for aberration compensation. Therefore, a fundus image is obtained smoothly and favorably.

It is to be noted that, when the control part 80 determines whether or not the circle 62 falls within the Hartmann image outer circumference 61*b*, the control part 80 may determine it is OK in a case where the position coordinates of the dot images on the Hartmann image outer circumference 61*b* are entirely outside or at the same positions as the position coordinates of the circle 62, and where the Hartmann image outer circumference 61*b* is in the circle 62. Further, the control part 80 may determine it is NG in a case where the position coordinates of any of the dot images on the Hartmann image outer circumference 61*b* are inside the position coordinates of the circle 62.

It is to be noted that the target pattern image need not fill 100% of the effective region to bring about OK in the above determination. In other words, wavefront aberration has only to be measured to a certain accuracy (for example, a case where the target pattern image fills 95% of the effective region (circle 62)). In a case where deviation is detected in a determination result (in a case of NG), the control part 80 controls the wavefront compensating device 72 to change the position of the effective region so that a portion larger than an allowable range (e.g., a portion having a certain percentage or more) in the effective region receives the target pattern image.

In the present embodiment, an aberration-compensating amount to be used after the position of the effective region is changed is fixed to an aberration-compensating amount before the position of the effective region is changed. However, the present disclosure is not limited thereto, and for example, aberration may be detected again after the position of the effective region is changed (specifically, compensation processing may be redone).

In the present embodiment, as for an aberration-compensating amount to be used immediately after the position of the effective region is changed (an initial value of the aberration-compensating amount in the feedback control after the position of the effective region is changed), the control part 80 does not reset it to zero but uses an aberration-compensating amount before the position of the effective region is changed.

Therefore, even in a case where the effective region is returned to an original position, the driving amount and driving time of the wavefront compensating device 72 are reduced. Thus, a fundus image is obtainable smoothly and favorably. It is to be understood that the control part 80 may reset the wavefront compensating device 72 to an initial state before starting aberration detection after the position of the effective region is changed.

In the present embodiment, after the position of the effective region is changed, the initial value of the aberration-compensating amount of the wavefront compensating device 72 is set to an aberration-compensating amount before the deviation information is out of the allowable range, and thereafter the feedback control is performed continuously. However, such control does not have to be performed.

In a case where the center of the measurable region deviates from the proximity of a detection optical axis L1 of the aberration detecting optical system 110, the control part 80 may cause the effective region 41 to be moved while the aberration-compensating amount is maintained and temporarily stop the feedback control. Moreover, the control part 80 may resume the feedback control in a case where the center of the measurable region is returned to the proximity of the detection optical axis L1.

For example, the control part 80 stores on the memory part 81 an aberration-compensating amount corresponding to the effective region 41 of the wavefront compensating device (wavefront aberration compensating device) 72 before deviation occurs. Thereafter, in a case where the center of the measurable region is returned to the proximity of the detection optical axis L1, the control part 80 returns the position of the effective region 41 and sets the aberration-compensating amount stored on the memory part 81 as an aberration-compensating amount of the wavefront compensating device 72.

Further, in the present embodiment, the control part 80 changes the position of the effective region to place the deviation information within the allowable range. However, such a configuration does not have to be provided. The changes in position of the effective region include a change in dimension or shape of the effective region. The deviation information is allowed to fall within the allowable range by such a change.

In the present embodiment, in a case where the effective region 41 (circle 62) deviates from the wavefront measuring region, the control part 80 controls the position of the effective region of the wavefront compensating device 72 to eliminate this deviation. However, the control part 80 is operable to eliminate the deviation without controlling the position of the effective region of the wavefront compensating device 72.

Figure 10:
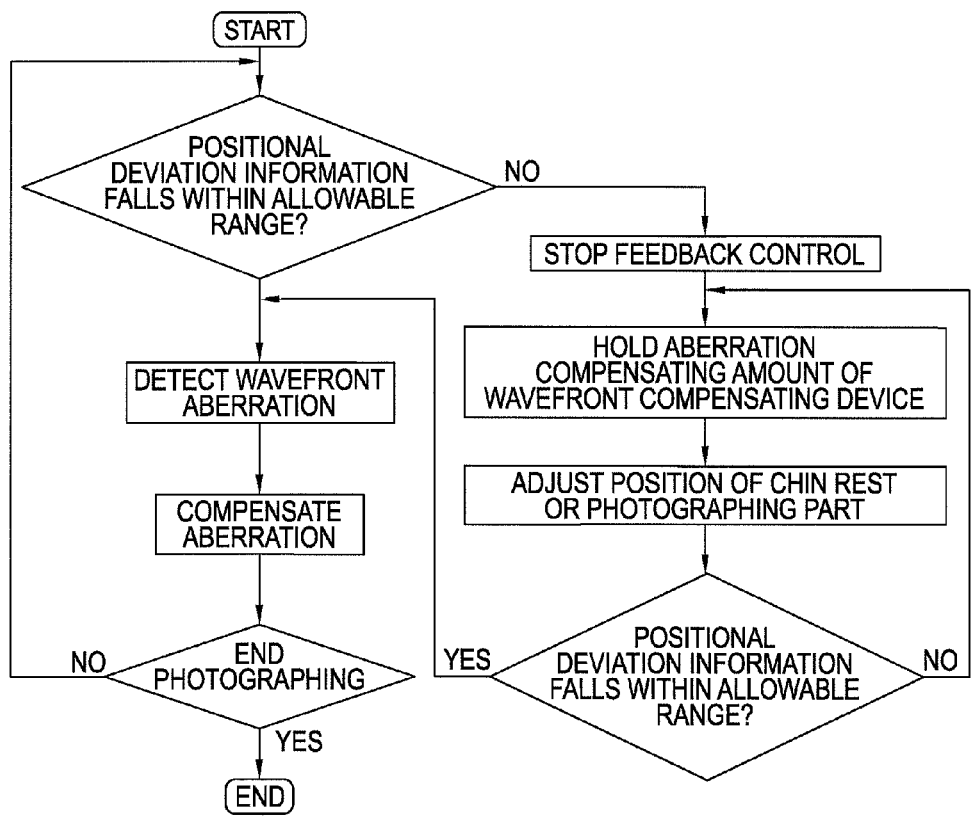
FIG. 10 is a flowchart of other operations of the fundus photographing apparatus.

Hereinafter, control operations for this case is described with reference to the flowchart in FIG. 10. In a case where the deviation information is out of the allowable range (for example, in a case where it is detected that the circle 62 deviates from the Hartmann image outer circumference 61*b*) after the wavefront compensating operation is started as described above, the control part 80 temporarily stops the above feedback control. The control part 80 continuously sets an aberration-compensating amount by the wavefront compensating device 72 to an aberration-compensating amount before the deviation information is out of the allowable range (for example, before the circle 62 deviates). The control part 80 also performs alignment (relative positional adjustment between the eye E and the photographing part 500) again so that the deviation information falls within the allowable range (for example, so that the circle 62 falls within the Hartmann image outer circumference 61*b*).

For example, the control part 80 does not send to the wavefront compensating device 72 driving signals based on an aberration detection result after the circle 62 deviates from the Hartmann image outer circumference 61*b*. The control part 80 continues to output to the wavefront compensating device 72 driving signals when the circle 62 falls within the outer circumference 61*b* (immediately before deviation or at a point in time prior to the deviation). The control part 80 operates the wavefront compensating device 72 with the same driving signals until the circle 62 falls within the outer circumference 61*b*. Furthermore, the wavefront compensating device 72 has only to be operated at an aberration-compensating amount on which an aberration detection result before the circle 62 deviates from the Hartmann image outer circumference 61*b* is reflected. In other words, similar driving signals to those before the circle 62 deviates from the Hartmann image outer circumference 61*b* have only to be applied to the wavefront compensating device 72.

In a case where the wavefront compensating device 72 is LCOS, the control part 80 has only to continuously set the voltage amount to be applied to pixels of the LCOS in order to keep the refractive index of the LCOS constant to the voltage amount before the circle 32 deviates from the Hartmann image outer circumference 31*a*. Similarly, in a case where the wavefront compensating device 72 is a deformable mirror, the control part 80 has only to continuously set the voltage amount to be applied to driving parts in order to keep the shape of the entire mirror constant to the voltage amount before the circle 32 deviates from the Hartmann image outer circumference 31*a*.

Even after the circle 62 deviates from the Hartmann image outer circumference 31a, the control part 80 operates the fundus photographing optical system 100 to obtain high-magnification images of the fundus successively. Additionally, the control part 80 outputs the obtained high-magnification images to the monitor 85 occasionally as moving images.

Further, the control part 80 controls the driving mechanism 505 to cause the photographing part 500 to be moved so that the circle 32 falls within the Hartmann image outer circumference 31a. Furthermore, depending on the fixation state of the eye E, there is a case in which alignment is naturally restored to a proper state.

When alignment is performed again in this manner, and it is detected that the circle 62 is returned to the inside of the Hartmann image outer circumference 61b, the control part 80 outputs a return signal to resume the feedback control. At this time, the control part 80 detects wavefront aberration by the wavefront sensor 73. Thus, the control part 80 obtains an aberration detection result after alignment is performed again. The control part 80 sends driving signals based on the aberration detection result to the wavefront compensating device 72. The control part 80 repeats the aberration detection by the wavefront sensor 73 and the wavefront compensation by the wavefront compensating device 72 based on the detection result while the circle 62 falls within the Hartmann image outer circumference 61b. Thus, an aberration detection result detected in real time is an aberration-compensating amount by the wavefront compensating device 72. Therefore, favorable high-magnification fundus images with less blur are obtained.

As described above, in a case where positional deviation between the examinee's eye E and the present apparatus (photographing part 500) occurs after the feedback control is started, the feedback control is temporarily stopped. Thus, wavefront compensation based on an aberration detection result at the time of generation of positional deviation is not performed. Therefore, a controlled portion (for example, the refractive index in a case of LCOS or the shape of a mirror in a case of a deformable mirror) of the wavefront compensating device 72 is prevented from being controlled with an erroneous aberration-compensating amount by the aberration detection result at the time of generation of fixation deviation. Further, a time from adjustment of positional deviation to resumption of appropriate wavefront compensation is shortened.

Further, after reexecution of alignment, the feedback control for aberration compensation is resumed with an aberration-compensating amount of the wavefront compensating device 72 in a previous alignment state as an initial value. Thus, the driving amount of the wavefront compensating device 72 can be small. Therefore, a fundus image is obtained smoothly and favorably. Further, even in a case where positional deviation occurs, the control state of the wavefront compensating device 72 remains in a state before generation of positional deviation. Thus, as long as positional deviation between the examinee's eye E and the present apparatus (photographing part 500) is minute, favorable high-magnification fundus images with less blur are obtained successively even when the circle 62 is deviated from the Hartmann image outer circumference 61b.

Furthermore, in a case where positional deviation occurs again after resumption of the feedback control, the control part 80 has only to perform stop and restoring operations of the feedback control in a similar manner.

It is to be noted that, in the present embodiment, the control part 80 continuously sets an aberration-compensating amount by the wavefront compensating device 72 when the circle 62 is deviated from the Hartmann image outer circumference 61b to an aberration-compensating amount before the circle 62 is deviated from the Hartmann image outer circumference 61b. However, the present disclosure is not limited thereto, and the control part 80 has only to resume the feedback control based on wavefront aberration detected appropriately.

For example, the control part 80 stores in the memory part 81 wavefront control information (data of an aberration-compensating amount) for a case where deviation information falls within the allowable range. Thereafter, in a case where the deviation information falls within the allowable range again, the control part 80 controls the wavefront compensating device 72 by using this wavefront control information.

To be specific, in a case where the circle 62 falls within the Hartmann image outer circumference 61b, the examiner or the control part 80 outputs a predetermined trigger signal. Thus, data of an aberration-compensating amount of the wavefront compensating device 72 is stored on the memory part 81. For example, an aberration-compensating amount of the wavefront compensating device 72 after several seconds have passed since the circle 32 falls within the Hartmann image outer circumference 61b is stored on the memory part 81. The aberration-compensating amount may be stored on the memory part 81 successively. Subsequently, any aberration-compensating amount may be selected from among the stored data.

Thereafter, in a case where the circle 62 deviates from the Hartmann image outer circumference 61b, the control part 80 temporarily stops the feedback control. Moreover, the control part 80 causes the photographing part 500 to be moved so that the circle 62 falls within the Hartmann image 61 again. When it is detected that the circle 62 is returned to the inside of the Hartmann image outer circumference 61b, the control part 80 outputs a return signal. Moreover, the control part 80 retrieves the data of the aberration-compensating amount of the wavefront compensating device 72 stored on the memory part 81 in advance and controls the wavefront compensating device 72 by use of it.

It is to be noted that, in the foregoing description, the control part 80 adjusts the position of the photographing part 500 to adjust a relative positional relation between the aberration detecting optical system 110 (photographing part 500) and the examinee's eye E. However, such a configuration does not have to be provided. The present apparatus has only to be configured to include a tracking system for adjusting the relative positional relation between the aberration detecting optical system 110 and the eye E so that the deviation information falls within the allowable range.

The control part 80 may cause the chin rest 610 to be moved with respect to the eye E so that, for example, deviation information falls within the allowable range. Further, the present apparatus may include an optical deflecting part for changing a traveling direction of a measurement light flux on the optical path of the detecting optical system 110. The control part 80 may drive this optical deflecting part to adjust a positional relation between the detecting optical system 110 and the examinee's eye E. It is to be noted that, in the present embodiment, the control part 80 detects deviation information corresponding to deviation between the effective region of the wavefront compensating device 72 and the detection region of the fundus reflection light flux in the wavefront sensor 73 based on an output signal of the wavefront sensor 73. However, the present disclosure is not limited thereto, and, in the present apparatus, the control part 80 has only to detect information corresponding to deviation between the effective region of the wavefront compensating device 72 and the wavefront measuring region with respect to a direction perpendicular to the optical axis.

For example, the present apparatus may include an observing optical system for observing an anterior segment front image of the examinee's eye. In this case, the control part 80 detects a pupil position from the anterior segment front image photographed by this observing optical system. Subsequently, the control part 80 detects information corresponding to deviation between the detected pupil position and the optical axis of the aberration detecting optical system 110 as deviation information.

It is to be noted that, in order to detect the pupil position, an effective region may be set on the anterior segment observing camera. In this case, the control part 80 may extract a pupil outer edge part by processing the anterior segment front image photographed by the anterior segment observing system. Further, the control part 80 may detect the pupil position based on the extracted pupil outer edge part.

Further, the present apparatus may include an alignment target light projecting optical system for forming an alignment target around a cornea by projecting alignment light to the examinee's eye and an alignment target detecting optical system for detecting the alignment target formed around the cornea. In this configuration, the control part 80 may render the alignment detection result detected by the anterior segment observing system correspond to the above-described deviation information in advance. The control part 80 may subsequently detect the pupil position indirectly based on the detection result from the alignment target detecting optical system. In this case, the control part 80 detects the pupil position indirectly, for example, on the premise that a corneal apex position detected from the alignment target and a pupil center position of a human eye are approximately at the same position.

The fundus photographing optical system 100 of the present apparatus may be a confocal optical system (SLO optical system). The SLO optical system receives a light flux reflected by the fundus of the examinee's eye through a confocal opening arranged approximately at a conjugate position with the fundus of the examinee's eye to photograph a confocal front image of the fundus of the examinee's eye. Further, the fundus photographing optical system 100 may be another optical system (for example, refer to JP-T-2001-507258).

The fundus photographing optical system 100 may be, for example, a fundus camera optical system. The fundus camera optical system receives a light flux reflected by the fundus of the examinee's eye on a two-dimensional imaging device to photograph a fundus front image of the examinee's eye. The fundus photographing optical system 100 may also be an optical interference optical system (OCT optical system). The OCT optical system receives interference light obtained by interference of a light flux reflected by the fundus of the examinee's eye with reference light to photograph a tomographic image of the examinee's eye.

Further, the fundus photographing apparatus (fundus photographing apparatus with wavefront compensation) according to the present embodiment may also be expressed as first to thirteenth fundus photographing apparatuses described below.

A first fundus photographing apparatus includes: a photographing optical system including a light source, an optical system for irradiating a fundus with light from the light source, and an optical system for receiving light reflected from the fundus and photographing a fundus image; a wavefront detecting optical system having a wavefront sensor for receiving light reflected from the fundus and measuring wavefront aberration of an eye; a wavefront compensating device disposed on an optical path of the photographing optical system for compensating the wavefront aberration by controlling a wavefront of incident light; and a deviation detecting part for detecting deviation information between an effective region in which control of aberration correction by the wavefront compensating device is effective, and a wavefront measuring region in which the wavefront aberration is measured by the wavefront detecting optical system, with respect to a direction perpendicular to an optical axial direction.

A second fundus photographing apparatus includes, in the first fundus photographing apparatus, a control unit for feeding a detection signal from the wavefront sensor back to the wavefront compensating device and controlling the wavefront compensating device under a closed loop condition to correct the wavefront aberration and temporarily stopping the feedback in a case where the deviation information detected at the deviation detecting part is out of an allowable range while resuming the feedback in a case where the deviation information is returned in the allowable range.

A third fundus photographing apparatus is adapted such that, in the second fundus photographing apparatus, the control unit holds in the wavefront compensating device an aberration-compensating amount before the deviation information is out of the allowable range when the control unit stops the feedback.

A fourth fundus photographing apparatus includes, in the second fundus photographing apparatus, a memory for storing wavefront control information of the wavefront compensating device, wherein the control unit stores on the memory the wavefront control information for a case where the deviation information falls within the allowable range and reflects the wavefront control information stored on the memory to the wavefront compensating device in a case where the deviation information is returned in the allowable range.

A fifth fundus photographing apparatus includes, in the first fundus photographing apparatus, a tracking system for relatively adjusting a positional relation between the wavefront detecting optical system and an examinee's eye so that the deviation information falls within the allowable range.

A sixth fundus photographing apparatus is adapted such that, in the fifth fundus photographing apparatus, the tracking system includes an optical deflecting part disposed on an optical path of the wavefront detecting optical system for changing a traveling direction of light and is adapted to drive the optical deflecting part to adjust the positional relation.

A seventh fundus photographing apparatus includes, in the first fundus photographing apparatus, a control unit for feeding a detection signal from the wavefront sensor back to the wavefront compensating device and controlling the wavefront compensating device under a closed loop condition to correct the wavefront aberration and adjusting a position of the effective region so that the deviation information falls within an allowable range in a case where the deviation information detected at the deviation detecting part is out of the allowable range.

An eighth fundus photographing apparatus is adapted such that, in the seventh fundus photographing apparatus, in a case where the control unit adjusts the position of the effective region, the control unit performs control for a second effective region after positional adjustment by using wavefront control information used in a first effective region before positional adjustment.

A ninth fundus photographing apparatus is adapted such that, in the eighth fundus photographing apparatus, the control unit temporarily stops the feedback in a case where the deviation information detected at the deviation detecting part is out of the allowable range and resumes the feedback after doing adjustment so that the effective region becomes the second effective region.

A tenth fundus photographing apparatus is adapted such that, in the first fundus photographing apparatus, the deviation detecting part detects, as the deviation information, deviation information between the effective region of the wavefront compensating device set on the wavefront sensor and a light-receiving region of light received by the wavefront sensor.

An eleventh fundus photographing apparatus includes, in the first fundus photographing apparatus, an observing optical system for observing an anterior segment front image of the examinee's eye and a pupil position detecting part for detecting a pupil position from the anterior segment front image photographed by the observing optical system, wherein the deviation detecting part detects, as the deviation information, deviation information between the pupil position detected by the pupil position detecting part and an optical axis of the wavefront detecting optical system.

A twelfth fundus photographing apparatus is adapted such that, in the eleventh fundus photographing apparatus , the pupil position detecting part extracts a pupil outer edge part by image processing from the anterior segment front image photographed by the observing optical system and detects the pupil position based on the extracted outer edge part.

A thirteenth fundus photographing apparatus includes, in the eleventh fundus photographing apparatus, a target light projecting optical system for forming an alignment target at a cornea by projecting alignment light to the examinee's eye and a target detecting optical system for detecting the alignment target formed at the cornea, wherein the pupil position detecting part detects the pupil position based on a detection result from the target detecting optical system.

The foregoing detailed description has been presented for the purposes of illustration and description. Many modifications and variations are possible in light of the above teaching. It is not intended to be exhaustive or to limit the subject matter described herein to the precise form disclosed. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims appended hereto.

What is claimed is:

1. A fundus photographing apparatus, comprising:
   a photographing optical system including:
      a first light source,
      an optical system for irradiating a fundus with light from the light source, and
      an optical system for receiving first reflection light from the fundus and photographing a fundus image;
   a wavefront detecting optical system including:
      a second light source for irradiating the fundus, and
      a wavefront sensor for receiving second reflection light from the fundus and measuring wavefront aberration of an eye;
   a wavefront compensating device disposed on an optical path of the photographing optical system for compensating the wavefront aberration by controlling a wavefront of incident light; and
   a deviation detecting part for detecting deviation information corresponding to deviation between an effective region and a wavefront measuring region with respect to a direction perpendicular to an optical axial direction, wherein aberration compensation by the wavefront compensating device is effective in the effective region and the wavefront aberration is measurable by the wavefront detecting optical system in the wavefront measuring region.

2. The fundus photographing apparatus according to claim 1, further comprising:
   a control unit for performing feedback control of the wavefront compensating device based on a detection signal from the wavefront sensor to compensate the wavefront aberration and temporarily stopping the feedback in a case where the deviation information detected at the deviation detecting part is out of an allowable range while resuming the feedback in a case where the deviation information is returned in the allowable range.

3. The fundus photographing apparatus according to claim 2, wherein the control unit is adapted to maintain an aberration-compensating amount of the wavefront compensating device to an aberration-compensating amount before the deviation information is out of the allowable range when the control unit stops the feedback.

4. The fundus photographing apparatus according to claim 2, further comprising:
   a memory for storing wavefront control information of the wavefront compensating device, wherein
   the control unit is adapted to store on the memory the wavefront control information for a case where the deviation information falls within the allowable range and to control the wavefront compensating device by using the wavefront control information to be stored on the memory in a case where the deviation information is returned in the allowable range.

5. The fundus photographing apparatus according to claim 1, further comprising:
   a tracking system for relatively adjusting a positional relation between the wavefront detecting optical system and an examinee's eye in such a manner that the deviation information falls within the allowable range.

6. The fundus photographing apparatus according to claim 5, wherein the tracking system includes an optical deflecting part disposed on an optical path of the wavefront detecting optical system for changing a traveling direction of light and is adapted to drive the optical deflecting part to adjust the positional relation.

7. The fundus photographing apparatus according to claim 1, further comprising:
   a control unit for performing feedback control of the wavefront compensating device based on a detection signal from the wavefront sensor to compensate the wavefront aberration and adjusting a position of the effective region in such a manner that the deviation information falls within an allowable range in a case where the deviation information detected at the deviation detecting part is out of the allowable range.

8. The fundus photographing apparatus according to claim 7, wherein, for adjusting the position of the effective region, the control unit is adapted to control the wavefront compensating device for a case where the effective region is a second effective region after positional adjustment by using wavefront control information for a case where the effective region is a first effective region before positional adjustment.

9. The fundus photographing apparatus according to claim 8, wherein the control unit is adapted to temporarily stop the feedback in a case where the deviation information detected at the deviation detecting part is out of the allowable range and to resume the feedback after performing adjustment such that the effective region is to be the second effective region.

10. The fundus photographing apparatus according to claim 1, wherein the deviation detecting part is adapted to detect, as the deviation information, information corresponding to deviation between a region of the wavefront sensor corresponding to the effective region of the wavefront compensating device and a light-receiving region of the wavefront sensor.

11. The fundus photographing apparatus according to claim 1, further comprising:
an observing optical system for observing an anterior segment front image of the examinee's eye; and
a pupil position detecting part for detecting a pupil position from the anterior segment front image to be photographed by the observing optical system, wherein
the deviation detecting part is adapted to detect, as the deviation information, deviation information corresponding to deviation between the pupil position to be detected by the pupil position detecting part and an optical axis of the wavefront detecting optical system.

12. The fundus photographing apparatus according to claim 11, wherein the pupil position detecting part is adapted to extract a pupil outer edge part by processing the anterior segment front image to be photographed by the observing optical system and to detect the pupil position based on the outer edge part to be extracted.

13. The fundus photographing apparatus according to claim 11, further comprising:
a target light projecting optical system for forming an alignment target at a cornea by projecting alignment light to the examinee's eye; and
a target detecting optical system for detecting the alignment target to be formed at the cornea, wherein
the pupil position detecting part is adapted to detect the pupil position based on a detection result from the target detecting optical system.

14. A fundus photographing apparatus, comprising:
a photographing optical system including
a plurality of light sources,
an optical system for irradiating a fundus with lights from the light sources, and
an optical system for receiving first reflection light from the fundus and photographing a fundus image;
a wavefront detecting optical system having a wavefront sensor for receiving second reflection light from the fundus and measuring wavefront aberration of an eye;
a wavefront compensating device disposed on an optical path of the photographing optical system for compensating the wavefront aberration by controlling a wavefront of incident light; and
a deviation detecting part for detecting deviation information corresponding to deviation between an effective region and a wavefront measuring region with respect to a direction perpendicular to an optical axial direction, wherein aberration compensation by the wavefront compensating device is effective in the effective region and the wavefront aberration is measurable by the wavefront detecting optical system in the wavefront measuring region.

15. The fundus photographing apparatus according to claim 14, further comprising:
a control unit for performing feedback control of the wavefront compensating device based on a detection signal from the wavefront sensor to compensate the wavefront aberration and temporarily stopping the feedback in a case where the deviation information detected at the deviation detecting part is out of an allowable range while resuming the feedback in a case where the deviation information is returned in the allowable range.

16. The fundus photographing apparatus according to claim 15, wherein the control unit is adapted to maintain an aberration-compensating amount of the wavefront compensating device to an aberration-compensating amount before the deviation information is out of the allowable range when the control unit stops the feedback.

17. The fundus photographing apparatus according to claim 15, further comprising:
a memory for storing wavefront control information of the wavefront compensating device, wherein
the control unit is adapted to store on the memory the wavefront control information for a case where the deviation information falls within the allowable range and to control the wavefront compensating device by using the wavefront control information to be stored on the memory in a case where the deviation information is returned in the allowable range.

18. The fundus photographing apparatus according to claim 14, further comprising:
a tracking system for relatively adjusting a positional relation between the wavefront detecting optical system and an examinee's eye in such a manner that the deviation information falls within the allowable range.

19. The fundus photographing apparatus according to claim 14, further comprising:
a control unit for performing feedback control of the wavefront compensating device based on a detection signal from the wavefront sensor to compensate the wavefront aberration and adjusting a position of the effective region in such a manner that the deviation information falls within an allowable range in a case where the deviation information detected at the deviation detecting part is out of the allowable range.

20. A fundus photographing apparatus, comprising:
a photographing optical system including:
a first light source,
an optical system for irradiating a fundus with light from the light source, and
an optical system for receiving first reflection light from the fundus and photographing a fundus image;
a wavefront detecting optical system including:
a second light source for irradiating the fundus, and
a wavefront sensor for receiving second reflection light from the fundus and measuring wavefront aberration of an eye;
a wavefront compensating device disposed on an optical path of the photographing optical system for compensating the wavefront aberration by controlling a wavefront of incident light; and
a control unit for performing feedback control by repeating detection of wavefront aberration of an examinee's eye based on a detection signal from the wavefront sensor and control of the wavefront compensating device based on the detection result, the control unit for resuming feedback control after controlling the wavefront compensating device using wavefront control information stored on a memory in advance.

* * * * *